(12) United States Patent
Murata et al.

(10) Patent No.: US 6,548,310 B1
(45) Date of Patent: Apr. 15, 2003

(54) PARTICLE FOR DIAGNOSTIC AGENT AND TURBIDMETRIC IMMUNOASSAY USING THE SAME

(75) Inventors: Mitsuhiro Murata, Ibaraki (JP); Satoshi Katayose, Ibaraki (JP); Kiyoshi Kasai, Mie (JP); Mikio Hikata, Ibaraki (JP); Toru Masukawa, Ibaraki (JP); Masaaki Kitajima, Kanagawa (JP)

(73) Assignee: JSR Corporation, Tokyo (JP)

( * ) Notice: Subject to any disclaimer, the term of this patent is extended or adjusted under 35 U.S.C. 154(b) by 0 days.

(21) Appl. No.: 09/495,318

(22) Filed: Feb. 1, 2000

(30) Foreign Application Priority Data

Jul. 8, 1999 (JP) ............................. 11-194372

(51) Int. Cl.⁷ ..................... G01N 33/543; G01N 33/545
(52) U.S. Cl. ..................... 436/518; 428/402; 428/403; 428/407; 436/528; 436/531; 436/532; 436/533; 436/534
(58) Field of Search ................. 428/402, 403, 428/407; 436/518, 528, 531, 532, 533, 534

(56) References Cited

U.S. PATENT DOCUMENTS

| | | | | |
|---|---|---|---|---|
| 4,181,636 A | * | 1/1980 | Fischer | 435/181 |
| 4,352,884 A | * | 10/1982 | Nakashima et al. | 435/180 |
| 4,962,154 A | * | 10/1990 | Pollock et al. | 525/54.1 |
| 5,043,062 A | * | 8/1991 | Bale et al. | 210/198.2 |
| 5,814,687 A | * | 9/1998 | Kasai et al. | 523/223 |

* cited by examiner

Primary Examiner—Christopher L. Chin
(74) Attorney, Agent, or Firm—Oblon, Spivak, McClelland, Maier & Neustadt, P.C.

(57) ABSTRACT

A particle for a diagnostic agent, which comprises a polymer particle comprising (A) from 20 to 100% by weight of a structural unit derived from at least one of acrylate having an aliphatic hydrocarbon group and methacrylate having an aliphatic hydrocarbon group, (B) from 0 to 10% by weight of a structural unit derived from unsaturated carboxylic acid, and (C) from 0 to 80% by weight of a structural unit derived from a vinyl monomer copolymerizable with the acrylate, methacrylate and unsaturated carboxylic acid, and a turbidmetric immunoassay using the same.

11 Claims, 2 Drawing Sheets

PARTICLE FOR DIAGNOSTIC AGENT AND TURBIDMETRIC IMMUNOASSAY USING THE SAME

BACKGROUND OF THE INVENTION

1. Field of the Invention

The present invention relates to particles for a diagnostic agent. More particularly, the present invention relates to particles for a diagnostic agent, which are used for the measurement of biochemical substances, especially in medical tests, and to a turbidmetric immunoassay using the same.

2. Description of the Background

As an important means in clinical laboratory tests, a method is used in which an immune response substance, such as an antibody, an antigen, or the like, or a nucleic acid is provided on carrier particles, and the corresponding substance to be tested, such as antigen, antibody, enzyme, nucleic acid, or the like, is detected by a specific reaction.

For example, when a dispersion of polymer particles on which an antibody has been provided by physical adsorption or chemical bonding is prepared, and a liquid to be tested containing an antigen corresponding to the antibody is added to the dispersion, the polymer particles aggregate due to changes in the surface conditions of the particles or due to formation of crosslinking between particles caused by an antigen-antibody specific bond.

Although such an aggregation of polymer particles can be observed with the naked eye on an appropriate plate, the substance to be tested (antigen) in a liquid sample is determined generally by measuring changes in turbidity of the liquid sample caused by the aggregation.

Examples of such a measuring system (determination method) include a method in which the changing rate of turbidity after addition of a liquid sample is measured (rate assay) and a method in which the subequilibrium turbidity after a lapse of a predetermined time after addition of a liquid sample is measured (end point assay).

Each of these methods uses a calibration curve prepared in advance by measuring a relationship between the amount of the substance to be tested (concentration) and the turbidity (changing rate or semiequilibrium turbidity).

In such a calibration curve, it is necessary that the absorbance of the substance to be treated is increased monotonously without a pro-zone region from its low concentration to high concentration, independent of the regularity of the gradient.

Polystyrene particles or carboxylic acid-modified styrene particles are known as polymer particles constituting particles for a diagnostic agent. Examples of the carboxylic acid which is used in a small amount to obtain the carboxylic acid-modified styrene particles include methacrylic acid, acrylic acid, itaconic acid, fumaric acid, and the like.

These polystyrene particles (polystyrene particles or carboxylic acid-modified styrene particles) become particles constituting a diagnostic agent as a result that antibodies or the like are sensitized. Also, a physiological saline supplemented with a substances necessary for adjusting the diagnostic agent performance is used as the medium of the diagnostic agents.

However, when the turbidity generated by the aggregation of polymer particles is measured based on the absorbance, the known polystyrene latex causes a problem in that its absorbance exceeds the measuring limit of a test apparatus even within a low concentration range of a substance to be tested due to its large absorbance even under unaggregated conditions (concentration of substance to be tested=0). Additionally, when the concentration of the polymer particles (latex concentration) is lowered to minimize the absorbance under unaggrigated conditions, a pro-zone phenomenon occurs at a high concentration region of the substance to be tested, so that considerable time and labor are required at the field of clinical laboratory tests, such as the necessity to carry out dilution of liquid samples.

In order to prevent generation of the pro-zone phenomenon in calibration curves by solving such problems, various resolving means, such as selection of antibodies etc., sensitization method, sensitization conditions, optimization of dispersion composition, and the like, have been examined, but satisfactory results have not been obtained.

Furthermore, as an approach from the material point of view for preventing generation of the pro-zone phenomenon in a calibration curve without exceeding the absorbance after aggregation over the measuring limit of a test apparatus, it has been proposed to use a fluorine-containing latex material which has a lower refraction index than that of the polystyrene latex (e.g., JP-A-61-247966, JP-A-63-200065, JP-A-63-278913 and JP-A-1-266111; the term "JP-A" as used herein means an "unexamined published Japanese patent application").

However, the fluorine-containing latex material has a problem in terms of production cost, for example, due to the necessity to use a pressure vessel for its production. Also, since the latex particles have a large specific gravity of at least 1.5, the material is poor in dispersion stability and therefore causes another problem in terms of storage stability. Moreover, it has still another problem in view of the difficulty in redispersion after centrifugation due to its low glass transition temperature (Tg) and in immobilizing an antigen or antibody by physical adsorption.

On the other hand, the development of polymer particles stained or dyed with a dyestuff or fluorescent material has been improved in order to improve visibility of the test results and detection sensitivity and to carry out measurement and inspection of a biochemical substance using the color or fluorescence of the polymer particles as a marker.

However, nothing is known about polymer particles constituting the particles for a diagnostic agent having good staining and dyeing properties.

SUMMARY OF THE INVENTION

An object of the present invention is to provide a novel particle for a diagnostic agent, which comprises a specific polymer as its constituting component.

Another object of the present invention is to provide particles for a diagnostic agent, which, when the turbidity generated by the aggregation of particles is measured based on the absorbance, show a low absorbance under unaggrigated conditions (concentration of substance to be tested=0), so that the absorbance does not exceed measuring limit of a test apparatus within a broad concentration range and it does not generate a pro-zone phenomenon even at a high concentration region in measuring a calibration curve of the concentration of a substance to be tested and the absorbance.

Furthermore, an object of the present invention is to provide particles for a diagnostic agent, which can measure a calibration curve having a broad concentration range of a substance to be tested without causing a pro-zone phenomenon, even when the sensitization treatment is carried out under standard conditions.

Moreover, an object of the present invention is to provide particles for a diagnostic agent having excellent staining and dyeing properties for a dye or a fluorescent material.

Also, an object of the present invention is to provide particles for a diagnostic agent, which can be used suitably in a test for determining a substance to be tested, in which the substance to be tested capable of specifically binding to an antigen, an antibody or a nucleic acid is added to an aqueous dispersion of particles whose surfaces are sensitized with the antigen, antibody or nucleic acid to aggregate the particles, and changes in the turbidity caused by the aggregation of the particles are measured.

The present invention relates to a particle for a diagnostic agent, which comprises a polymer particle (hereinafter referred to as "specific (co)polymer") comprising (A) from 20 to 100% by weight of a structural unit derived from at least one of acrylate having an aliphatic hydrocarbon group and methacrylate having an aliphatic hydrocarbon group (hereinafter referred to as "structural unit (A)"), (B) from 0 to 10% by weight of a structural unit derived from unsaturated carboxylic acid (hereinafter referred to as "structural unit (B)"), and (C) from 0 to 80% by weight of a structural unit derived from a vinyl monomer copolymerizable with the acrylate, methacrylate and unsaturated carboxylic acid (hereinafter referred to as "structural unit (C)").

Furthermore, the present invention relates to a process for producing the above particle for a diagnostic agent, which comprises polymerizing in water a monomer comprising (A) from 20 to 100% by weight of at least one member selected from the group consisting of acrylate having an aliphatic hydrocarbon group of 20 or less carbon atoms and methacrylate having an aliphatic hydrocarbon group of 20 or less carbon atoms, (B) from 0 to 10% by weight of unsaturated carboxylic acid, and (C) from 0 to 80% by weight of a vinyl monomer copolymerizable with the acrylate, methacrylate and unsaturated carboxylic acid to obtain a water dispersion of a polymer particle; and alkalizing the water dispersion, followed by heating.

Moreover, the present invention relates to a turbidmetric iummunoassay which comprises mixing a substance to be tested with the above particle for a diagnostic agent having thereon a biochemical substance capable of specifically reacting with the substance to be tested to aggregate the particle for a diagnostic agent, and measuring an absorbance of the resulting mixture.

DETAILED DESCRIPTION OF THE INVENTION

Figure 1:
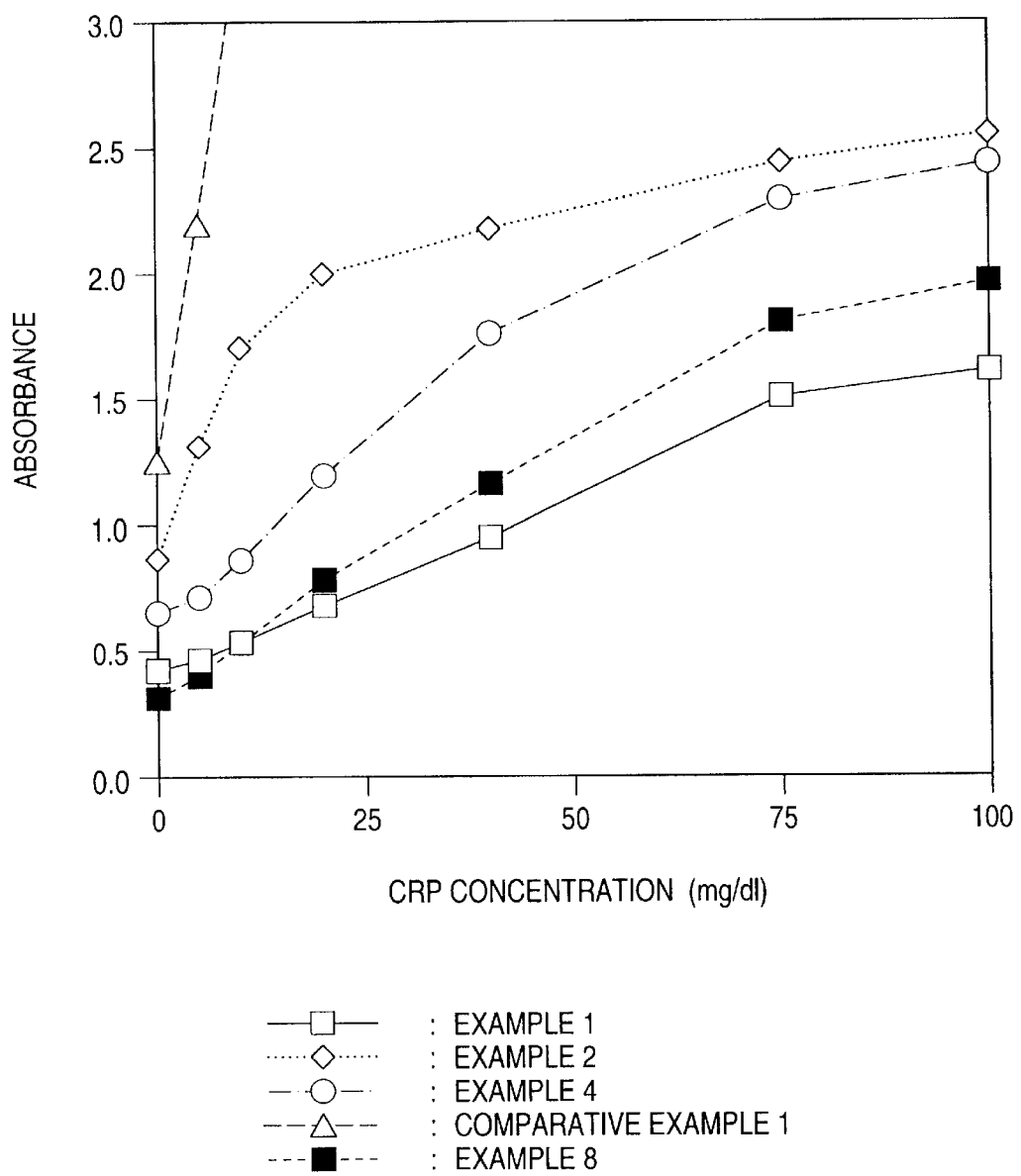
FIG. 1 is a calibration curve obtained by measuring a CRP antigen by an end point assay using particles for a diagnostic agent sensitized with an anti-CRP antibody.

The particles for a diagnostic agent of the present invention use the specific (co)polymer (specific copolymer or specific polymer) as its constituting component.

Examples of the acrylate having an aliphatic hydrocarbon group or the methacrylate having an aliphatic hydrocarbon group (hereinafter referred to as "monomer (A)") which is used for obtaining the structural unit (A) constituting the specific (co)polymer include alkyl (meth)acrylates having a chain structure alkyl group, such as methyl acrylate, methyl methacrylate, ethyl acrylate, ethyl methacrylate, propyl acrylate, propyl methacrylate, n-butyl acrylate, n-butyl methacrylate, t-butyl acrylate, t-butyl methacrylate, isobutyl acrylate, isobutyl methacrylate, pentyl acrylate, pentyl methacrylate, 2-ethylhexyl acrylate, 2-ethylhexyl methacrylate, stearyl acrylate, stearyl methacrylate, lauryl acrylate, lauryl methacrylate, and the like; (meth)acrylates having a cyclic aliphatic group, such as cyclohexyl acrylate, cyclohexyl methacrylate, cyclohexyl ethylene glycol methacrylate, cyclohexyl dipropylene glycol methacrylate, and the like; and substituted cyclohexyl (meth)acrylates and cyclohexyl di(meth)acrylate in which a part of hydrogen atoms of the cyclohexyl group is substituted with an alkyl group having 1 to 4 carbon atoms, such as methyl-substituted cyclohexyl acrylate, and the like. These monomers may be used alone or as a combination of two or more.

Among these monomers (A), acrylates and methacrylates having an aliphatic hydrocarbon group of preferably from 1 to 20, more preferably from 4 to 20, carbon atoms, such as 2-ethylhexyl acrylate, t-butyl methacrylate, cyclohexyl methacrylate, cyclohexyl acrylate, substituted cyclohexyl acrylate, substituted cyclohexyl methacrylate, and the like, are preferred, and (meth)acrylates having a cyclic aliphatic hydrocarbon group, such as cyclohexyl methacrylate, cyclohexyl acrylate, substituted cyclohexyl acrylate, substituted cyclohexyl methacrylate, and the like, are particularly preferred because of their low nonspecific adsorption and excellent storage stability.

The amount of the structural unit (A) in the specific (co)polymer is generally from 20 to 100% by weight, preferably from 65 to 100% by weight. When the amount of the structural unit (A) is at least 20% by weight, the particles for a diagnostic agent show excellent adsorption property and binding reactivity with an immune response substance (e.g., antibody).

The unsaturated carboxylic acid (hereinafter referred to as "monomer (B)") which is used for obtaining the structural unit (B) constituting the specific copolymer is a polymerizable monomer having a radical-polymerizable unsaturated bond and a carboxyl group in the molecule.

Examples of the monomer (B) include acrylic acid, methacrylic acid, crotonic acid, itaconic acid, fumaric acid, maleic acid, and the like. These acids may be used alone or as a combination of two or more.

The amount of the structural unit (B) in the specific copolymer is generally from 0 to 10% by weight, preferably from 0 to 5% by weight.

The particles for a diagnostic agent constituting the specific copolymer into which the structural unit (B) has been introduced are mainly subjected to sensitization treatment by chemical bonding, and the particles for a diagnostic agent into which the structural unit (B) has not been introduced are mainly subjected to sensitization treatment by physical adsorption.

Examples of the vinyl monomer (hereinafter referred to as "monomer (C)") which is used for obtaining the structural unit (C) constituting the specific copolymer include aromatic vinyl compounds, such as styrene, α-methylstyrene, vinyltoluene, divinylbenzene, styrenesulfonic acid, and the like; (meth)acrylates having an alkyl group of from 1 to 3 carbon atoms, such as methyl acrylate, methyl methacrylate, ethyl acrylate, ethyl methacrylate, isopropyl acrylate, isopropyl methacrylate, and the like; and vinyl ester compounds, such as vinyl acetate and the like. These compounds may be used alone or as a combination of two or more.

The amount of the structural unit (C) in the specific copolymer is generally from 0 to 80% by weight, preferably from 0 to 35% by weight.

The specific copolymer can be obtained by polymerizing the above monomer (A), monomer (B) and optionally monomer (C) (hereinafter referred to as "specific monomers") in water, for example, by emulsion polymerization, suspension polymerization, dispersion polymerization, or the like.

According to the present invention, it is preferred to use a persulfuric acid salt as the initiator in polymerizing the specific monomers.

Although the persulfuric acid salt is not particularly limited in the present invention, potassium persulfate, sodium persulfate, ammonium persulfate or the like may be preferably used in an amount of from 0.01 to 5% by weight based on the specific monomers.

In the present invention, an anionic, nonionic, cationic emulsifier or the like can also be used when the specific monomers are polymerized.

The polymerization of the specific monomers in the present invention is carried out with stirring at a temperature of from 50 to 100° C., preferably from 60 to 90° C., for 5 to 50 hours In the present invention, after completion of the polymerization of the specific monomers, the water dispersion of the specific particles is adjusted to a pH of from 7 to 12, preferably from 8 to 11, by dissolving therein an appropriate amount of an alkaline compound, such as a hydroxide, a oxide, a carbonate, a bicarbonate or the like of an alkali metal or an alkaline earth metal, or the like, specifically, sodium hydroxide, potassium hydroxide, sodium carbonate, or the like, and then heated to a temperature of from 50 to 100° C., preferably from 50 to 90° C., for 1 to 50 hours, preferably for 10 to 50 hours.

If necessary, the particles for a diagnostic agent thus obtained in the present invention can be purified by an optional method, such as centrifugation, dialysis, or the like.

The particles for a diagnostic agent of the present invention may be either polymer particles solely constituted by the specific (co)polymer or composite particles in which a layer of the specific (co)polymer is continuously or intermittently formed on the surface of core particles made of a material other than the specific (co)polymer. The polymer particles solely constituted the specific (co)polymer are preferred in view of easy production. Also, examples of the material constituting the core particles include polystyrene, carboxyl group-modified polystyrene, silica, and the like.

It is preferred that the particles for a diagnostic agent of the present invention are non-magnetic particles which are free of a super paramagnetic substance.

The particle size of the particles for a diagnostic agent of the present invention is not particularly limited, but it is preferred that they have an average particle size d (number average particle size) of preferably from 0.03 to 10 μm, more preferably from 0.05 to 1 μm.

If the average particle size d is too small, measuring sensitivity of a substance to be tested at a low concentration range may be insufficient. On the other hand, if the average particle size d is too large, measuring sensitivity of a substance to be tested at a high concentration range may be insufficient.

Furthermore, the term "average particle size d (nm)" as used herein means a number average particle size obtained by taking electron microphotographs of the particles with a transmission electron microscope, and measuring the size of at least 200 randomly selected particles.

Also, when the average particle size of the particles for a diagnostic agent of the present invention is defined as d (nm) and the absorbance of a water dispersion of the particles for a diagnostic agent having a solid content of 0.05 w/v % measured at a wavelength of 600 nm is defined as A, it is preferred that conditions shown in the following formula (1), more preferably the following formula (2), are satisfied:

$$A < f(d) = (M_0 + M_1 d + M_2 d^2 + M_3 d^3 + M_4 d^4) \quad (1)$$

wherein $M_0 = 0.012573$, $M_1 = -0.0020732$, $M_2 = 6.33 \times e^{-5}$, $M_3 = -8.7935 \times e^{-8}$, and $M_4 = 3.529 \times e^{-11}$.

When the particles for a diagnostic agent satisfy the conditions of the above formula (1), the absorbance under unaggrigated conditions becomes lower than that of a polystyrene latex, so that the absorbance within a broad concentration range can be measured by a test apparatus when a calibration curve of the concentration of a substance to be tested versus the absorbance is measured. Also, the absorbance of known polystyrene latexes always becomes f(d) or more when measured under the same conditions:

$$A < k \cdot f(d) \quad (2)$$

wherein, k is less than 1, preferably 0.95 or less, and more preferably 0.90 or less.

The particles for a diagnostic agent of the present invention may comprise polymer particles of the specific (co) polymer and other polymer particles having a refraction index of from 1.57 to 1.65.

Examples of the polymer particles having a refraction index of from 1.57 to 1.65 include polystyrene particles, crosslinked polystyrene particles, and carboxylic acid-modified styrene polymer particles. Examples of the carboxylic acid which is used in a small amount to obtain the carboxylic acid-modified styrene polymer particles include methacrylic acid, acrylic acid, itaconic acid, fumaric acid, and the like.

Furthermore, the average particle size of the polymer particles is preferably from 0.04 to 0.5 μm.

Also, the polymer particles of the specific (co)polymer and the particles having a refraction index of from 1.57 to 1.65 may be subjected to sensitization as their mixture or be used by mixing them after separate sensitization.

Generally, the particles for a diagnostic agent of the present invention has thereon a biochemical substance when used.

Examples of the biochemical substance include an antigen, an antibody, an enzyme, a nucleic acid, and the like. The method for sensitizing the particles for a diagnostic agent with a biochemical substance is not particularly limited, and chemical bonding is mainly applied to the particles for a diagnostic agent constituted by the specific copolymer having the structural unit (B), and physical adsorption is mainly applied to the particles for a diagnostic agent constituted by the specific copolymer which is free of the structural unit (B).

The antigen or antibody to be provided on the particles for a diagnostic agent of the present invention is not particularly limited, so long as it can react with a component generally contained in a substance to be tested (substance to be tested in a liquid sample). The examples thereof include antigens or antibodies for aggregation and fibrinolysis-related inspections, such as antiplasmin antibody for antiplasmin inspection, D dimer antibody for D dimer inspection, anti-FDP antibody for FDP inspection, anti-tPA antibody for tPA inspection, anti-thrombin/antithrombin complex antibody for TAT inspection, anti-FPA antibody for FPA inspection, and the like; antigens or antibodies for tumor-related inspections, such as anti-BFP antibody for BFP inspection, anti-CEA antibody for CEA inspection, anti-AFP antibody for AFP inspection, anti-ferritin antibody for ferritin inspection, anti-CA19-9 antibody for CA19-9 inspection, and the like; antigens or antibodies for serum protein-related inspections, such as anti-apolipoprotein antibody for apolipoprotein inspection, anti-β2-microglobulin antibody for β2-microglobulin inspection, anti-α1-microglobulin antibody for α1-microglobulin inspection, anti-immunoglobulin antibody for immunoglobulin inspection, anti-CRP antibody for CRP inspection, and the like; antigens or antibodies for endocrine function inspections, such as anti-HCG antibody for HCG inspection and the like; antigens or antibodies for infectious disease-related inspections, such as anti-HBs antibody for HBs antigen inspection, HBs antigen for HBs antibody inspection, HCV antigen for HCV antibody inspection, HIV-1 antigen for HIV-1 antibody inspection, HIV-2 antigen for HIV-2 antibody inspection, HTLV-1 antigen for HTLV-1 antibody inspection, mycoplasma antigen for mycoplasma disease inspection, toxoplasma antigen for toxoplasma inspection, streptolysin 0 antigen for ASO inspection, and the like; antigens or antibodies for autoimmune-related inspections, such as DNA antigen for anti-DNA antibody inspection, heat-denatured human IgG for RF inspection, and the like; and antigens or antibodies for drug analyses, such as anti-digoxin antibody for digoxin inspection, anti-lidocaine antibody for lidocaine inspection, and the like. The antibodies may be either polyclonal antibodies or monoclonal antibodies.

In the turbidmetric immunoassay of the present invention, a buffer dispersion of the particles for a diagnostic agent having thereon an antigen or antibody (hereinafter referred to as "sensitized particles") are mixed with a substance to be tested to aggregate the sensitized particles.

In this case, the concentration of the sensitized particles as solid in the buffer dispersion is generally from 0.001 to 1.0% by weight.

Examples of the buffer include those having such a pH and an ionic strength that they do not exert influences upon the substance to be tested and antigen-antibody reaction, such as a phosphate buffer, a Tris buffer, a glycine buffer, a HEPES buffer, and the like.

Also, it is preferred to add a substance to be tested to the buffer dispersion of the sensitized particles in an amount of from 0.05 to 5% by weight.

In the turbidmetric immunoassay of the present invention, the sensitized particles is allowed to react with a substance to be tested at a pH of from 5 to 10, preferably from 6 to 8, and at a reaction temperature of from 0 to 50° C., preferably from 20 to 40° C. The reaction time is optionally decided.

When aggregation of the sensitized particles is generated in the turbidmetric immunoassay of the present invention, the reaction can be carried out in the presence of at least one of an aggregation accelerator and a nonspecific aggregation inhibitor.

Examples of the aggregation accelerator in the present invention include water-soluble high polymers having a molecular weight of from 500 to 2,000,000, preferably from 500 to 1,000,000, such as polyvinyl pyrrolidone, polyethyleneimine, polyethylene glycol, CHAPS (3-[(3-cholamidopropyl)dimethylammonio]-1-propane-sulfonic acid), BIGCHAP (N,N-bis(3-D-gluconamidopropyl)-cholamide), digitonin, saponin, pullulan, polyglycosylethyl methacrylate, and the like. Among these, polyethylene glycol and digitonin are preferred.

Examples of the nonspecific aggregation inhibitor include proteins, such as gelatin, albumin, and the like; glycols; polyanions; N,N-dialkylamides; lower alkyl sulfoxides; nitrates, such as potassium nitrate, sodium nitrate, lithium nitrate, barium nitrate, calcium nitrate, ammonium nitrate, and the like; and thiocyanates, such as potassium thiocyanate, sodium thiocyanate, lithium thiocyanate, barium thiocyanate, calcium thiocyanate, ammonium thiocyanate, and the like.

The above-described aggregation accelerator and nonspecific aggregation inhibitor may be used in combination.

In the turbidmetric immunoassay of the present invention, an assay kit constituted by two liquid reagents, namely a suspension of the sensitized particles and a buffer as the medium of an antigen-antibody reaction, is generally provided.

In the measurement of the aggregation, the concentration of the substance to be tested is measured by conducting the aggregation using the above reagent and optically observing the degree of the resulting aggregation.

Specifically, the aggregation of the sensitized particles of the present invention is measured using an optical apparatus which can measure a scattered light intensity, a transmittance or a transmitted light intensity. The measuring wavelength is preferably from 300 to 2400 nm. The measurement is carried out by setting a particle size and concentration of the sensitized particles and a reaction time and measuring the increased or decreased degree of a scattered light intensity, a transmittance or a transmitted light intensity.

There are two turbidity measuring methods, namely a rate assay in which the changing rate of turbidity after addition of a liquid sample (substance to be tested) is measured and an end point assay in which the semiequilibrium turbidity after a lapse of a predetermined time after addition of a liquid sample (substance to be tested) is measured. Among these, the rate assay is preferred.

(1) According to the present invention, a novel particle for a diagnostic agent comprising a specific polymer as its constituting component can be provided.

(2) According to the particles for a diagnostic agent of the present invention, they show a low absorbance under unaggrigated conditions so that the absorbance does not exceed a measuring limit of a test apparatus within a broad concentration range and a pro-zone phenomenon is not generated even at a high concentration region in measuring a calibration curve of the concentration of a substance to be tested and the absorbance.

(3) According to the particles for a diagnostic agent of the present invention, a calibration curve having a broad concentration range of a substance to be tested can be measured without causing the pro-zone phenomenon even when the sensitization treatment is carried out under standard conditions.

(4) The particles for a diagnostic agent of the present invention have excellent staining and dyeing properties of a dye or a fluorescent material, and the stained or dyed particles can show excellent visibility of aggregation in inspections and, when a fluorescent dye is used, the determination sensitivity can be markedly improved by carrying out a fluorescence measurement.

(5) The particles for a diagnostic agent of the present invention can be used suitably in inspections for the determination of a substance to be tested by adding a substance to be tested capable of specifically binding to an antigen, an antibody or a nucleic acid to an aqueous dispersion of particles whose surfaces are sensitized with the antigen, the antibody or the nucleic acid to aggregate the above-described particles, and measuring changes in the turbidity caused by the aggregation of the particles.

(6) Since the particles for a diagnostic agent of the present invention require no special apparatus (e.g., pressure vessel) for their production, it is advantageous from the viewpoint of the production apparatus and the production cost.

(7) In a diagnostic agent prepared from the particles for a diagnostic agent of the present invention, the constituting particles (particles after the sensitization treatment) have good storage stability so they hardly aggregate after their storage for a prolonged period of time, as compared with particles obtained by sensitizing a known polystyrene latex and the like. This is an important characteristic for the quality control of diagnostic agents and is a great advantage from the viewpoint of the quality maintenance of products of the diagnostic agents.

(8) The particles for a diagnostic agent of the present invention are low in so-called nonspecific adsorption, namely adsorption of physiologically active substances other than the antibody or antigen for the sensitized antigen or antibody.

Examples of the present invention are given below by way of illustration; however, the present invention is not limited thereto. Hereinafter, unless otherwise indicated, "part(s)" means "part(s) by weight".

EXAMPLES 1 TO 7 AND COMPARATIVE EXAMPLE 1

A 5 liter glass flask equipped with a stirrer was charged with 100 parts of each of the monomers shown in Table 1, 500 parts of water, 1 part of potassium persulfate and 0.2 part of sodium dodecylbenzenesulfate, and the polymerization reaction was carried out at 80° C. for 6 hours in a nitrogen atmosphere to prepare a suspension of polymer particles (particles for a diagnostic agent of the present invention or comparative particles for a diagnostic agent).

The conversion ratio was at least 98% in each polymerization reaction system.

The average particle size d of the thus obtained polymer particles is also shown in Table 1.

EXAMPLE 8

Polymer particles were obtained in the same manner as in Example 1, and, after completion of the polymerization, the atmosphere in the reaction vessel was replaced by air and the reaction solution was adjusted to pH 8.4, followed by stirring at 70° C. for 24 hours. The particle size of the thus obtained particles was 0.18 $\mu$m.

Conditions of Formula (1)

In order to know whether each of the preparations of polymer particles (particles for a diagnostic agent) obtained in Examples 1 to 8 and Comparative Example 1 satisfies the conditions (A<f(d)) shown in the above-described formula (1), the absorbance A at a wavelength of 600 nm of each of the water dispersions of the particles for a diagnostic agent having a solid concentration of 0.05 w/v % was measured. The results A are also shown in Table 1.

Evaluation of Dye-affinity

To 100 ml of 1% by weight water dispersion of each of the preparations of polymer particles (particles for a diagnostic agent) obtained in Examples 1 to 8 and Comparative Example 1, 10 ml of a 2% by weight Congo Red toluene solution and 1 g of sodium dodecylbenzene sulfonate as an emulsifier were added, and the resulting mixture was thoroughly dispersed by ultrasonic dispersion, followed by stirring at 80° C. for 3 hours for staining treatment of the polymer particles. After cooling, toluene was removed by steam stripping, and the polymer particles were collected by filtration and purified by removing the unadhered dye through 4 times repeated centrifugation/redispersion treatment. The dye-affinity of the polymer particles after purification was evaluated by the following five step evaluation.

Evaluation:
1: Faintly stained
2: Slightly stained
3: Moderately stained
4: Sufficiently stained
5: Quite sufficiently stained.

The results are also shown in Table 1.

Range of Calibration Curve

Each of the preparations of the polymer particles (particles for a diagnostic agent) obtained in Examples 1 to 8 and Comparative Example 1 was dispersed in a mixed solution of 1 part by volume of a 1/15 M phosphate buffer (pH 7.2) and 3 parts by volume of a phosphate buffered saline (hereinafter referred to as "PBS") to give a polymer particle concentration of 1% by weight, and the dispersion was mixed with the same volume of 1 mg/ml solution of an anti-CRP antibody (rabbit) and kept at 56° C. for 30 minutes for sensitization treatment. After the sensitization treatment, unsensitized antibody molecules were removed by dialysis and gel filtration, and the particle concentration was adjusted to 0.13% by weight by adding a dilution solution (PBS containing 0.1% bovine serum albumin) to obtain an anti-CRP antibody-sensitized latex diagnostic agent.

Performance of each of the thus obtained anti-CRP antibody-sensitized latex diagnostic agent was evaluated by measuring a calibration curve in the following manner using a CRP antigen standard solution.

As a result, the pro-zone phenomenon was not generated by the substance to be tested within a broad concentration range of from 0 to 100 mg/dl in the calibration curves related to Examples 1 to 8.

Apparatus: Hitachi 7020 Automatic Analyzer
Wavelength: 570 rm, Measuring temperature : 37° C.
Tested substance (0–100 mg/dl CRP standard solution) 3 $\mu$l
First reagent (PBS containing 0.1% bovine serum albumin): 200 $\mu$l
Second reagent (latex diagnostic agent): 200 $\mu$l The calibration curve was measured by the rate assay by mixing and stirring the above substance to be tested, first reagent and second reagent and then measuring a difference (changing amount) between the turbidity after a lapse of time of 50 seconds and the turbidity after a lapse of time of 200 seconds.

TABLE 1

Unit of blended amount: part(s)

| Monomers | Examples | | | | | | | | Comp. Ex. |
| --- | --- | --- | --- | --- | --- | --- | --- | --- | --- |
| | 1 | 2 | 3 | 4 | 5 | 6 | 7 | 8 | 1 |
| A Cyclohexyl methacrylate | 100 | 75 | 51 | 77 | 78 | | | 100 | |
| A t-Butyl methacrylate | | | | | | 75 | | | |
| A 2-Ethylhexyl acrylate | | | | | | | 60 | | |
| B Acrylic acid | | | | | 1 | | | | |
| B Methacrylic acid | | | | 3 | | | | | |
| B Itaconic acid | | | | | 1 | | | | |
| C Styrene | | 25 | 49 | 20 | 20 | 25 | 40 | | 100 |
| Alkali treatment | no | no | no | no | no | no | no | yes | no |
| Average particle size D (µm) | 0.17 | 0.24 | 0.37 | 0.21 | 0.14 | 0.19 | 0.11 | 0.17 | 0.18 |
| Conditions of formula (1) f(d) | 1.34 | 2.95 | 7.59 | 2.19 | 0.84 | 1.74 | 0.45 | 1.34 | 1.53 |
| Conditions of formula (1) Absorbance A | 0.61 | 1.28 | 5.85 | 0.94 | 0.36 | 0.67 | 0.30 | 0.61 | 1.53 |
| Dye-affinity Index | 5 | 5 | 4 | 4 | 4 | 5 | 4 | 5 | 1 |
| Pro-zone | absent | absent | absent | absent | absent | absent | absent | absent | present |

Application Example of Diagnostic Drugs

Each of the preparations of polymer particles (particles for a diagnostic agent) obtained in Examples 1, 2, 4 and 8 and Comparative Example 1 was sensitized with anti-CRP antibody to obtain an anti-CR v antibody-sensitized latex diagnostic agent. Performance of each of the thus obtained anti-CRP antibody-sensitized latex diagnostic agent was evaluated by measuring a calibration curve in the following manner using CRP antigen standard solution.

Apparatus: Hitachi 7020 Automatic Analyzer

Wavelength: 600 nm, Measuring temperature: 370°

Tested substance (0–100 mg/dl CRP standard solution): 3 µl

First reagent (PBS-containing 0.1% bovine serum albumin): 200 µl

Second reagent (latex diagnostic agent): 200 µl

MEASUREMENT EXAMPLE 1 (END POINT ASSAY)

Each of the preparations of particles for a diagnostic agent obtained in Examples 1, 2, 4 and 8 and Comparative Example 1 (0.1 w/v %) was sensitized with the anti-CRP antibody, and the calibration curve was obtained by mixing and stirring the above substance to be tested, first reagent and second reagent and then measuring the absorbance after a lapse of time of 211 seconds. The results are shown in FIG. 1.

As shown in FIG. 1, when the particles for a diagnostic agent of Comparative Example 1 was used, the initial turbidity was high and exceeded the measuring limit of the testing instrument (absorbance=3) even at a low CRP concentration, so that it was impossible to carry out the measurement at higher concentrations. When the preparations of particles for a diagnostic agent obtained in Examples 1, 2, 4 and 8 were used, the initial turbidity was low and it was able to carry out the measurement even at high CRP concentrations without exceeding the measuring limit of the testing instrument.

MEASUREMENT EXAMPLE 2 (RATE ASSAY)

Each of the preparations of particles for a diagnostic agent obtained in Examples 1, 2 and 4 and Comparative Example 1 (0.15 w/v %) was sensitized with the anti-CRP antibody, and the calibration curve was obtained by the rate assay by mixing and stirring the above substance to be tested, first reagent and second reagent and then measuring a difference (changing amount) between the turbidity after a lapse of time of 36 seconds and the turbidity after a lapse of time of 126 seconds. The results are shown in FIG. 2.

Figure 2:
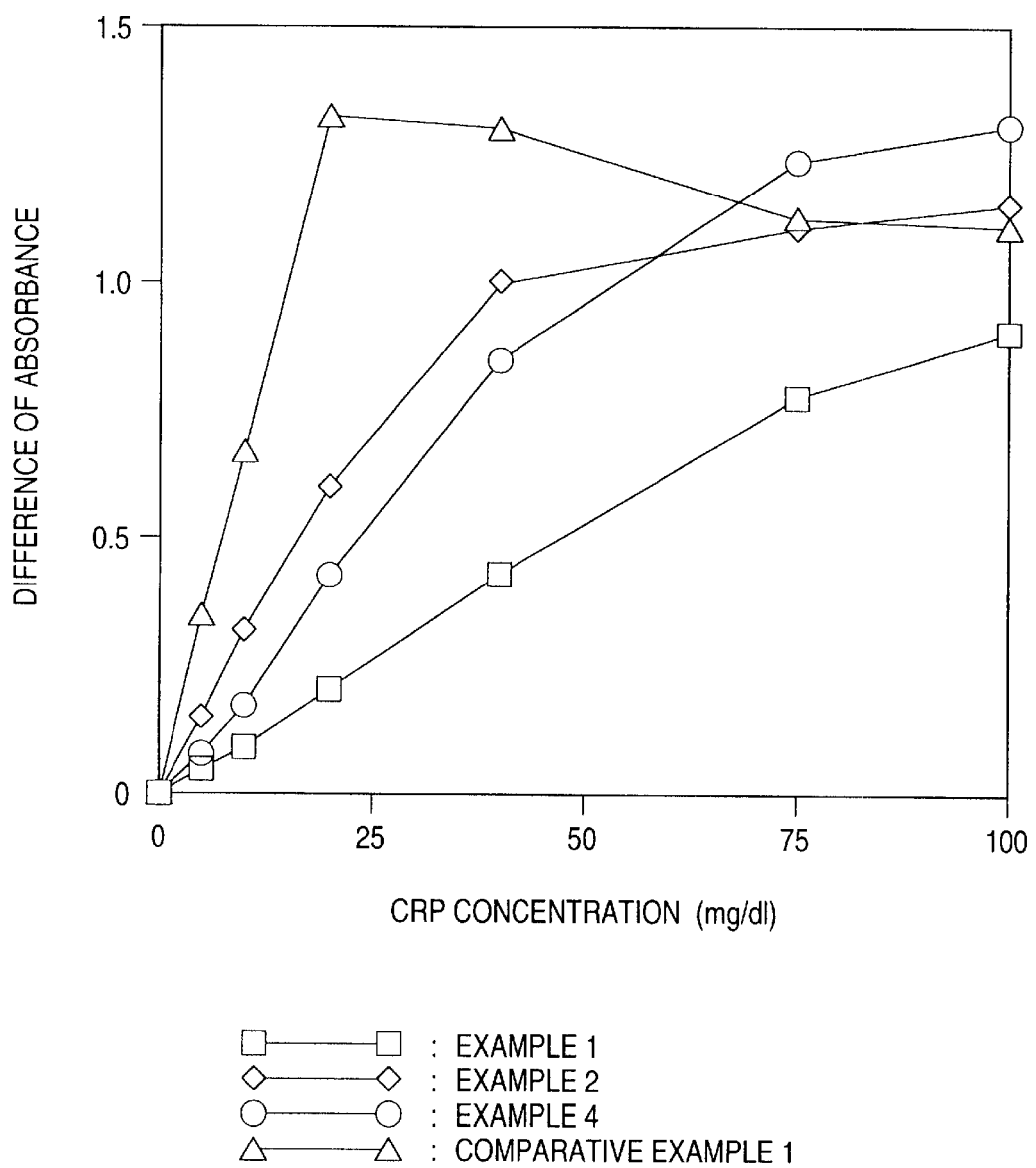
FIG. 2 is a calibration curve obtained by measuring a CRP antigen by a rate assay using particles for a diagnostic agent sensitized with an anti-CRP antibody.

As shown in FIG. 2, the pro-zone phenomenon was observed when the particles for a diagnostic agent of Comparative Example 1 was used, but was not observed when the preparations of particles for a diagnostic agent of Examples 1, 2 and 4 were used.

Detection of AFP Antibody by Sensitized Fluorescent Particles

Fluorescent particles were obtained by dyeing the polymer particles obtained in Example 4 with eosin as a fluorescent dye. The thus obtained fluorescent particles were dispersed in PBS to give a concentration of 1% by weight, and the dispersion was mixed with the same volume of a 1 mg/ml solution of an anti-AFP antibody (mouse) and kept at 56° C. for 30 minutes for the sensitization treatment. After the sensitization treatment, unsensitized antibody molecules were removed by dialysis and gel filtration, and the particle concentration was adjusted to 0.1% by weight by adding a dilution solution (PBS containing 0.1% bovine serum albumin) to obtaining anti-AFP antibody-sensitized fluorescent particles.

On the other hand, 0.1 mg of non-fluorescent magnetic particles on which an anti-AFP antibody (mouse) capable of recognizing other epitope had been immobilized were mixed with 500 ng/ml AFP solution to bind AFP to the non-fluorescent magnetic particles in advance, and then 1 mg of the above anti-AFP antibody-sensitized fluorescent particles were added to the thus prepared mixture and incubated at 37° C. for 10 minutes. By this treatment, the fluorescent particles were further bound to the AFP antibody-bonded magnetic particles via AFP.

Thereafter, the magnetic particles were separated by magnetic separation and washed three times with the dilution solution, and then the fluorescence intensity of the magnetic particle dispersion was measured by a fluorospectrophotometer. As a result, the fluorescence intensity when 500 ng/ml of AFP was used was 120 times higher than the case of fluorescence intensity in which AFP was not used. Based on this result, it was able to detect the AFP antibody bonded to the magnetic particles using the fluorescent particles of the present invention as a marker.

While the invention has been described in detail and with reference to specific examples thereof, it will be apparent to one skilled in the art that various changes and modifications can be made therein without departing from the spirit and scope thereof.

The priority applications, Japanese patent application No. Hei 11-194372, filed Jul. 8, 1999, is incorporated herein by reference in its entirety.

What is claimed is:

1. A non-magnetic particle for a diagnostic agent, which comprises a non-magnetic polymer particle comprising:
   (A) from 65 to 100% by weight of cyclohexyl acrylate or cyclohexyl methacrylate,
   (B) from 0 to 10% by weight of a structural unit derived from unsaturated carboxylic acid, and
   (C) from 0 to 35% by weight of a structural unit derived from a vinyl monomer copolymerizable with the acrylate, methacrylate and unsaturated carboxylic acid.

2. A The particle for a diagnostic agent according to claim 1, wherein it satisfies conditions shown in the following formula (1):

$$A < f(d) = (M_0 + M_1 d + M_2 d^2 + M_3 d^3 + M_4 d^4) \quad (1)$$

wherein d is an average particle size (rm) of the polymer particle; A is an absorbance of a water dispersion of the polymer particles at a solid content of 0.05 w/v %, when measured at a wavelength of 600 nm; and $M_0 = 0.012573$, $M_1 = -0.0020732$, $M_2 = 6.33 \times e^{-5}$, $M_3 = -8.7935 \times e^{-8}$ and $M_4 = 3.529 \times e^{-11}$.

3. The particle for a diagnostic agent according to claim 1, wherein the particle has thereon a biochemical substance.

4. The particle for a diagnostic agent according to claim 1, which further comprises a polymer particle having a refraction index of from 1.57 to 1.65.

5. The particle for a diagnostic agent according to claim 4, wherein the polymer particle having a refraction index of from 1.57 to 1.65 is at least one selected from the group consisting of a polystyrene particle, a crosslinked polystyrene particle, and a carboxylic acid-modified styrene polymer particle.

6. The particle according to claim 4, wherein said polymer particle has an average particle size of 0.04 to 0.5 μm.

7. The particle according to claim 1, wherein (B) is selected from the group consisting of acrylic acid, methacrylic acid, crotonic acid, itaconic acid, fumaric acid, maleic acid, and combinations thereof.

8. The particle according to claim 1, wherein (B) is present in an amount of 0 to 5% by weight.

9. The particle according to claim 1, wherein (C) is selected from the group consisting of styrene, α-methylstyrene, vinyl toluene, divinylbenzene, styrenesulfonic acid, methyl methacrylate, methyl acrylate, ethyl acrylate, ethyl methacrylate, isopropyl methacrylate, vinyl acetate, and combinations thereof.

10. The particle according to claim 1, having a number average particle size of 0.03 to 10 μm.

11. The particle according to claim 1, having a number average particle size of 0.05 to 1 μm.

* * * * *